(12) United States Patent
Duncan

(10) Patent No.: US 10,265,148 B2
(45) Date of Patent: Apr. 23, 2019

(54) ORAL CARE SYSTEM AND ORAL CARE DEVICE

(71) Applicant: COLGATE-PALMOLIVE COMPANY, New York, NY (US)

(72) Inventor: Kelly Gail Duncan, Washington, NJ (US)

(73) Assignee: Colgate-Palmolive Company, New York, NY (US)

( * ) Notice: Subject to any disclaimer, the term of this patent is extended or adjusted under 35 U.S.C. 154(b) by 182 days.

(21) Appl. No.: 15/309,189

(22) PCT Filed: May 7, 2014

(86) PCT No.: PCT/US2014/037159
§ 371 (c)(1),
(2) Date: Nov. 6, 2016

(87) PCT Pub. No.: WO2015/171134
PCT Pub. Date: Nov. 12, 2015

(65) Prior Publication Data
US 2017/0065387 A1    Mar. 9, 2017

(51) Int. Cl.
*A61C 17/22* (2006.01)
*A46B 11/00* (2006.01)
(Continued)

(52) U.S. Cl.
CPC .......... *A61C 17/227* (2013.01); *A46B 5/0095* (2013.01); *A46B 9/04* (2013.01);
(Continued)

(58) Field of Classification Search
CPC ..... A46B 5/0095; A46B 9/04; A46B 11/0003; A46B 11/00; A46B 11/0006;
(Continued)

(56) References Cited

U.S. PATENT DOCUMENTS 3,593,725 A    7/1971  Ortega
4,503,871 A *  3/1985  Mendenhall ............. A46B 5/00
                                                           132/311
(Continued)

FOREIGN PATENT DOCUMENTS

CN      2914805 Y     6/2007
CN    201194628 Y     2/2009
(Continued)

OTHER PUBLICATIONS

International Search Report and the Written Opinion of the International Searching Authority issued in international application PCT/US2014/037159 dated Feb. 2, 2015.

*Primary Examiner* — David J Walczak

(57) ABSTRACT

An oral care system comprising: an oral care implement, comprising: a body comprising a handle and a head at an end of the handle, the head having at least one oral care element extending therefrom, and a cavity in the body, the body defining an opening of the cavity; and a plurality of dentifrice-free oral care devices in the cavity, each of the oral care devices comprising an oral care composition comprising an oral care agent. The oral care device may comprise a storage portion comprising a sealed vessel having an interior holding an oral care composition comprising an oral care agent; and an applicator connected to the storage portion; wherein the vessel or a seal thereof is breakable to place the interior of the vessel in fluid communication with the applicator.

13 Claims, 2 Drawing Sheets

(51) Int. Cl.
*A46B 5/00* (2006.01)
*A46B 9/04* (2006.01)

(52) U.S. Cl.
CPC ...... *A46B 11/0003* (2013.01); *A46B 11/0006* (2013.01); *A46B 11/0072* (2013.01); *A46B 2200/1066* (2013.01)

(58) Field of Classification Search
CPC .............. A46B 11/001; A46B 11/0072; A46B 11/0013; A46B 11/0062; A46B 11/0068; A46B 2200/1066
See application file for complete search history.

(56) References Cited

U.S. PATENT DOCUMENTS

| | | | | |
|---|---|---|---|---|
| 4,740,194 | A | * | 4/1988 | Barabino ................ A61F 13/38 401/132 |
| 5,098,297 | A | * | 3/1992 | Chari .................. A61M 35/006 401/132 |
| 5,755,020 | A | | 5/1998 | Panyon |
| 6,283,933 | B1 | * | 9/2001 | D'Alessio ........... A61M 35/003 401/132 |
| 8,328,451 | B1 | | 12/2012 | Atkin |
| 8,523,475 | B2 | | 9/2013 | Jimenez et al. |
| 2005/0137110 | A1 | | 6/2005 | Ghosh et al. |
| 2006/0159509 | A1 | | 7/2006 | Grez et al. |

FOREIGN PATENT DOCUMENTS

| | | |
|---|---|---|
| CN | 202653478 U | 1/2013 |
| WO | 2004056287 | 7/2004 |
| WO | WO2011/111081 | 9/2011 |
| WO | WO2014/062186 | 4/2014 |

* cited by examiner

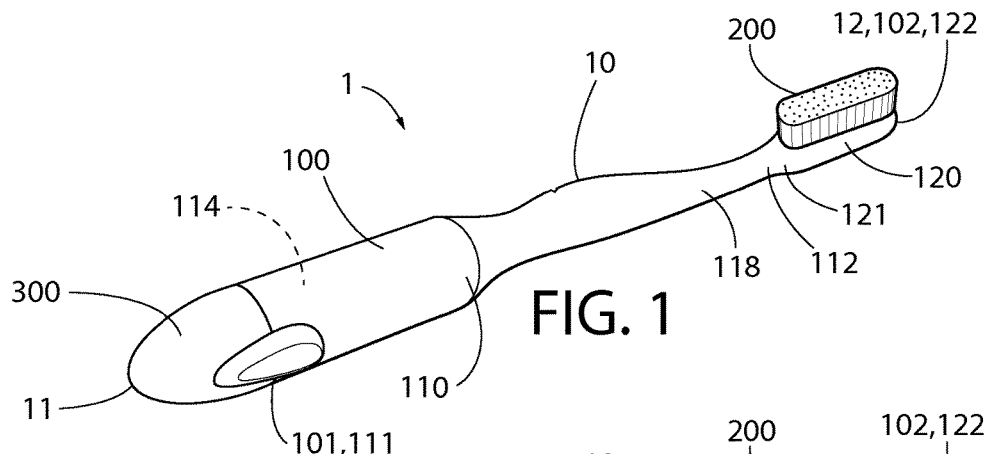
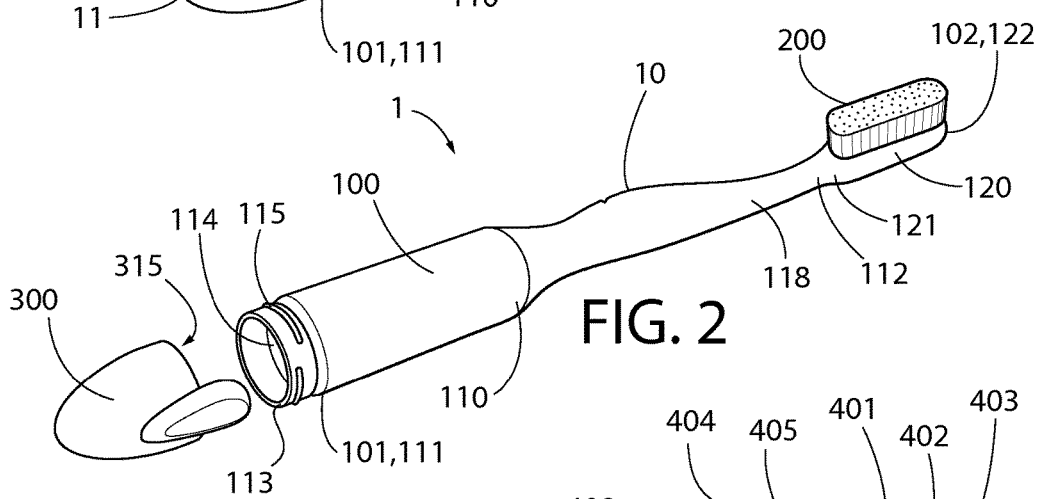
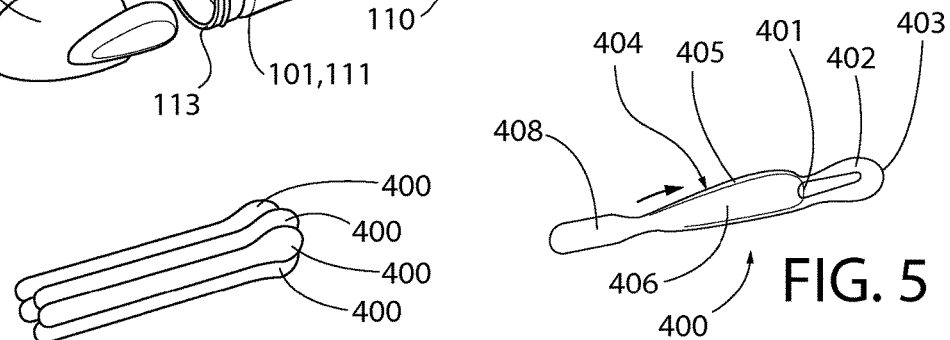
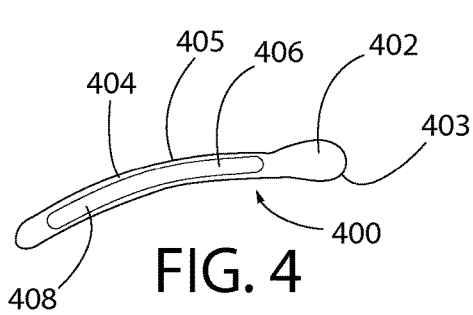
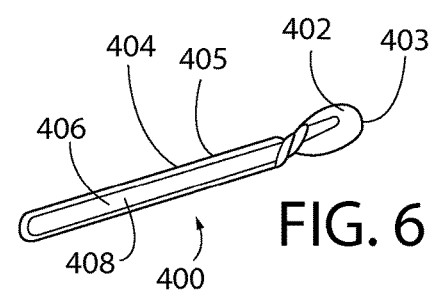

ORAL CARE SYSTEM AND ORAL CARE DEVICE

BACKGROUND

The present invention relates to an oral care system comprising an oral care implement, such as a toothbrush, and an oral care device storing an oral care composition comprising an oral care agent, such as a whitening agent. The present invention also relates to an oral care device holding an oral care composition comprising an oral care agent, such as a whitening agent.

It is known to provide an oral care device that is operable to dispense an oral care composition comprising an oral care agent to a user's teeth. Some known such oral care devices are difficult to operate to dispense a suitable, small volume of the oral care composition. This can result in application of a volume of the oral care agent to a user's teeth greater than a volume actually required for the oral care agent to have the desired effect, such as teeth whitening. Accordingly, some of the oral care composition is wasted. In some cases, it is preferable not to apply too great a volume of a particular oral care agent, such as a whitening agent, to a user's teeth. It is also known to provide an oral care system comprising an oral care implement, such as a toothbrush, within which is stored such an oral care device. However, while these systems are convenient in that they provide a compact structure comprising both an oral care implement and an oral care device, typically the oral care devices of the systems still suffer from the above problem that they are difficult to operate to dispense a suitable volume of the oral care composition.

There is a need for an oral care system that is more easily operable to provide a user with a suitable volume of an oral care composition comprising an oral care agent. There also is a need for an oral care device that is more easily operable to provide a user with a suitable volume of an oral care composition comprising an oral care agent.

BRIEF SUMMARY

An embodiment of the present invention provides an oral care system, comprising: an oral care implement, comprising: a body comprising a handle and a head at an end of the handle, the head having at least one oral care element extending therefrom, and a cavity in the body, the body defining an opening of the cavity; and a plurality of dentifrice-free oral care devices in the cavity, each of the oral care devices comprising an oral care composition comprising an oral care agent.

Optionally, each of the oral care devices comprises a predetermined dose or volume of the oral care agent comprised in the oral care device.

Optionally, each of the oral care devices comprises the same oral care composition. Further optionally, each of the oral care devices comprises an equal predetermined dose of the oral care agent.

Optionally, each of the oral care devices is a single-use device.

Optionally, each of the oral care devices is sealed to isolate the oral care composition from an exterior of the oral care device. Further optionally, each of the oral care devices is sealed by a removable lid, film or sheet, to isolate the oral care composition from an exterior of the oral care device.

Optionally, the plurality of dentifrice-free oral care devices comprises a plurality of strips holding the oral care composition.

Optionally, each of the oral care devices comprises a vessel, within an interior of which the oral care composition is held. Further optionally, each of the vessels comprises a tray or a tube.

Optionally, each of the oral care devices comprises a storage portion comprising a sealed vessel having an interior holding an oral care composition comprising an oral care agent; and an applicator; wherein the vessel or a seal thereof is breakable to place the interior of the vessel in fluid communication with the applicator.

Optionally, the vessel comprises a tube. Further optionally, the storage portion comprises an impermeable outer tube disposed around an inner tube, and wherein the interior is an interior of the inner tube.

Optionally, the applicator is made from a porous material.

Optionally, the applicator comprises a member with one or more channels defined therein for carrying the oral care composition.

Optionally, material of the oral care device is twistably deformable, in order to place the interior of the vessel in fluid communication with the applicator.

Optionally, the vessel is snappable, in order to place the interior of the vessel in fluid communication with the applicator.

Optionally, the oral care composition is in the form of one of a paste, a gel, a liquid, a flowable material, and a powder.

Optionally, the oral care agent is selected from the group consisting of: antibacterial agents; oxidative or whitening agents; enamel strengthening or repair agents; tooth erosion preventing agents; tooth anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof.

Optionally, the oral care implement comprises a cap movable relative to the body between a first position, at which the cap blocks the opening, and a second position, at which the opening is not blocked by the cap.

Optionally, the cap is detached from the body when the cap is at the second position.

Optionally, the cap is attached to the body when the cap is at the second position. Further optionally, the cap is attached to the body via a hinge.

Optionally, the oral care implement is a toothbrush.

Another embodiment of the present invention provides an oral care device, comprising: a storage portion comprising a sealed vessel having an interior holding an oral care composition comprising an oral care agent; and an applicator connected to the storage portion; wherein the vessel or a seal thereof is breakable to place the interior of the vessel in fluid communication with the applicator.

Optionally, the oral care device is dentifrice-free.

Optionally, the oral care composition comprises a dentifrice.

Optionally, the oral care composition is in the form of one of a paste, a gel, a liquid, a flowable material, and a powder.

Optionally, the oral care agent is selected from the group consisting of: antibacterial agents; oxidative or whitening agents; enamel strengthening or repair agents; tooth erosion preventing agents; tooth anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof.

Optionally, the vessel comprises a tube. Further optionally, the storage portion comprises an impermeable outer tube disposed around an inner tube, and wherein the interior is an interior of the inner tube.

Optionally, the applicator is made from a porous material.

Optionally, the applicator comprises a member with one or more channels defined therein for carrying the oral care composition.

Optionally, material of the oral care device is twistably deformable, in order to place the interior of the vessel in fluid communication with the applicator.

Optionally, the vessel is snappable, in order to place the interior of the vessel in fluid communication with the applicator.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 shows a perspective view of an oral care system according to an exemplary embodiment of the present invention, with a cap of an oral care implement of the system at a first position relative to the body so that the cap blocks an opening of a cavity in the body;

FIG. 2 shows a perspective view of the oral care system of FIG. 1, with the cap at a second position relative to the body so that the cap does not block the opening of a cavity;

FIG. 3 shows a perspective view of a plurality of oral care devices of the system of FIG. 1, bundled together as they would be stored in the cavity of the oral care implement;

FIG. 4 shows a perspective view of one of the oral care devices of FIG. 3 after an inner tube of the device has been broken;

FIG. 5 shows a perspective view of an alternative oral care device for use in the system of FIG. 1;

FIG. 6 shows a perspective view of another alternative oral care device for use in the system of FIG. 1;

DETAILED DESCRIPTION

Figure 7:
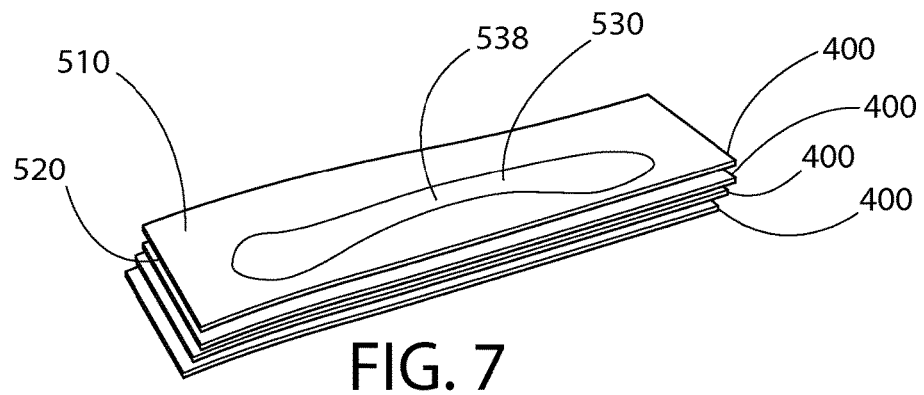
FIG. 7 shows a perspective view of a stack of alternative oral care devices for use in the system of FIG. 1.

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

In the following description, each of the exemplary embodiments of the oral care system of the invention comprises a manually-operated oral care implement, more specifically a manually-operated toothbrush. However, in variations to these embodiments, the oral care system could instead comprise a powered oral care implement, such as a powered toothbrush, wherein one or more oral care elements provided to the head of the implement are drivable so as to be moved relative to the handle of the implement. In still further embodiments, the oral care system could instead comprise other forms of oral care implement, such as a soft-tissue cleaner, a tooth polisher, an interdental brush, a tongue scraper, or another implement designed for oral care. It is to be understood that other embodiments may be utilised, and that structural and functional modifications may be made without departing from the scope of the present invention.

FIGS. 1 and 2 illustrate an oral care system according to an exemplary embodiment of the present invention, generally designated with the reference numeral 1. The system 1 comprises an oral care implement, in this case a toothbrush, 10 and a plurality of dentifrice-free oral care devices 400. The toothbrush 10 generally comprises a body 100, oral care elements 200 on a head 120 of the body 100, a cap 300 at a proximal end 101 of the body 100, and a cavity 114 within which the oral care devices 400 are stored.

The body 100 of the toothbrush 10 has the proximal end 101 and a distal end 102 and is elongate between the proximal and distal ends 101, 102. The body 100 comprises a handle 110 and a head 120 at a distal end 112 of the handle 110. The head 120 is a distal portion of the body 100 and has a proximal end 121 and a distal end 122, which distal end 122 forms the distal end 102 of the body 100. The head 120 has extending therefrom oral care elements 200 for cleaning or polishing surfaces in a user's mouth, such as surfaces of their teeth. In FIGS. 1 and 2, the oral care elements 200 are illustrated as a simple block for clarity. However, it will be appreciated that, in reality, the oral care elements 200 comprise a plurality of individually identifiable oral care elements.

The oral care elements 200 extend from a first, front side of the toothbrush 10 and are for cleaning or polishing surfaces in a user's mouth, such as surfaces of their teeth. As used herein, the term "oral care element" is used in a generic sense to refer to any structure that can be used to clean, massage or polish an oral surface, such as teeth or soft tissue, through relative surface contact. In this embodiment, the oral care elements comprise a plurality of tooth cleaning elements, preferably a plurality of flexible, nylon bristles arranged in tufts. However, in variations to this embodiment, the oral care elements may additionally or alternatively comprise one or more tooth polishing elements, preferably in the form of elastomeric tooth polishing elements, such as elastomeric protrusions, elements, fingers, or prophylactic (prophy) cups. In some embodiments, the oral car elements 200 may comprise at least one of any one or more of the following, without limitation: bristles, rigid bristles, flexible bristles, filament bristles, fibre bristles, nylon bristles, spiral bristles, rubber bristles, elastomeric protrusions, elastomeric elements, flexible polymer protrusions, co-extruded filaments, flag bristles, crimped bristles, anti-bacterial bristles and combinations thereof and/or structures containing such materials or combinations.

In a variation to the illustrated embodiment, a soft tissue cleaner may be provided on a second side of the toothbrush 10, such as a rear side of the toothbrush 10 opposite to the front side of the toothbrush 10. Such a soft tissue cleaner may be provided on an opposite side of the head 120 from the at least one oral care element 200.

The handle 110 is a proximal portion of the body 100 and has the distal end 112 and a proximal end 111, which proximal end 111 forms the proximal end 101 of the body 100. The handle 110 includes a neck portion 118 by which the handle 110 is connected with the head 120. The neck portion 118 is generally of a smaller cross sectional area than the rest of the handle 110. The neck portion 118 includes the distal end 112 of the handle 110, which is that portion of the handle 110 fixed to and closest to the proximal end 121 of the head 120. In the illustrated embodiment, the head 120 is non-detachable from the handle 110. However, in variations to the illustrated embodiment, the head 120 may be detachable from the handle 110, such as for replacement of the head 110 when the oral care elements 200 become worn.

The handle 110 provides a user with a mechanism by which he/she can readily grip and manipulate the toothbrush 10, includes ergonomic features which provide a high degree of control for the user while maintaining comfort, and may be formed of many different shapes and with a variety of constructions. Although the handle 110 is a non-linear structure in the illustrated embodiment, the invention is not so limited, and in certain embodiments the toothbrush 10 may have a simple linear handle 110.

A cavity 114 is provided in the handle 110 of the body 100 and the handle 110 defines an opening 113 of the cavity 114 at the proximal end 111 of the handle 110. In the illustrated embodiment, the opening 113 is the only access path into the cavity 114 from an exterior of the toothbrush 10.

The cap 300 of the toothbrush 10 is non-unitary with the body 100 and is usable for blocking the opening 113 defined by the body 100. The cap 300 is movable relative to the body 100 between the first position (see FIG. 1), at which the cap 300 blocks the opening 113, and a second position (see FIG. 2), at which the opening 113 is not blocked by the cap 300. In the illustrated embodiment, when the cap 300 is at the first position relative to the body 100, a proximal end 11 of the toothbrush 10 is defined by the cap 300, a distal end 12 of the toothbrush 10 is the distal end 102 of the body 100, and the body 100 and the cap 300 cooperate to isolate the cavity 114 from the exterior of the toothbrush 10. When the cap 300 is at the second position relative to the body 100, the cap 300 is detached from the body 100 and the cavity 114 is in fluid communication with the exterior of the toothbrush 10.

The body 100 and the cap 300 comprise respective co-operable couplers 115, 315 for coupling the cap 300 to the body 100 when the cap 300 is at the first position relative to the body 100. More specifically, in the illustrated embodiment, the respective co-operable couplers 115, 315 comprise respective co-operable threads 115, 315 on respective surfaces of the body 100 and the cap 300. In variations to the illustrated embodiment, the respective co-operable couplers comprise a protrusion protruding radially outwardly from one of the proximal end of the body 100 and the cap 300 and a depression within the other of the proximal end of the body 100 and the cap 300, the cap 300 is couplable to the body 100 by pressing the cap 300 in the direction of the body 100 with the protrusion aligned with the depression so that the protrusion "snaps" into the depression, and the cap 300 is decoupleable from the body 100 by pulling the cap 300 in a direction away from the body 100 with sufficient, yet small, force to "pop" the protrusion out from the depression. Other suitable co-operable couplers for use in embodiments of the present invention will be apparent to the skilled person.

The oral care system 1 further comprises the plurality of single-use dentifrice-free oral care devices 400 in the cavity 114 of the toothbrush 10, each of which oral care devices 400 comprises an oral care composition comprising an oral care agent. The oral care devices 400 in isolation, and the manner in which they are stackable together in the cavity 114, is shown in FIG. 3. The oral care composition is free of (i.e., is not) dentifrice, such as toothpaste, and is intended to provide supplemental oral care benefits in addition to merely brushing one's teeth. The oral care composition may be in any form such as a solid or a flowable material including, without limitation, viscous pastes/gels or less viscous liquid compositions. Preferably, the oral care composition is a flowable material. Any suitable oral care agent can be used in the present invention. For example, in each of the embodiments illustrated in FIGS. 3 to 9, the oral care agent is a whitening agent, such as, without limitation, a peroxide containing tooth whitening composition. However, in respective variations to those embodiments, the oral care agent is selected from the group consisting of: antibacterial agents; oxidative or whitening agents; enamel strengthening or repair agents; tooth erosion preventing agents; tooth anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof.

In the illustrated embodiments, each of the oral care devices 400 in the cavity 114 is single-use, dentifrice-free and comprises the same oral care composition. Moreover, each of the oral care devices 400 comprises an equal predetermined dose or volume of the oral care agent, which preferably is a dose sufficient for the oral care agent to have the desired effect, such as teeth whitening. Accordingly, a user easily is able to apply an appropriate dose of the oral care agent to the appropriate surface in their oral cavity, without wasting the oral care composition and without having to carefully measure-out the oral care composition.

In order to use the oral care system 1 of FIG. 1, the user applies a dentifrice to the oral care elements 200 and then uses the dentifrice and the oral care elements 200 to brush their teeth. In order to benefit from the effects of the oral care agent comprised in the oral care composition of one of the oral care devices 400 in the cavity 114, before, during or after brushing their teeth, the user moves the cap 300 relative to the body 100 from the first position to the second position to access the cavity 114 through the opening 113, and removes one of the oral care devices 400 from the cavity 114. The user then moves the cap 300 relative to the body 100 back to the first position, so that the cap 300 seals the opening 113, and the body 100 and the cap 300 co-operate to isolate the cavity 114, the oral care devices 400, and the oral care agent(s) held by the oral care devices 400, from the exterior of the toothbrush 10. Accordingly, the oral care agent(s) held by the oral care devices 400 are well preserved during periods of non-use.

The manner in which the oral care device 400 is used by the user depends on the type of oral care device 400 present in the cavity 114. In the embodiment of FIGS. 1 to 3, each of the oral care devices 400 comprises an applicator 402, and a storage portion 404 connected to the applicator 402 and comprising a substantially impermeable outer tube 405 disposed around a sealed but breakable inner vessel, in the form of a tube 406, within which inner tube 406 the oral care composition 408 is held. Since the inner tube 406 is sealed, the oral care composition 408 is isolated from an exterior of the oral care device 400.

In order to use one of the oral care devices 400 of FIG. 3, a user applies a force to the inner tube 406 of the oral care device 400 in order to snap or break the inner tube 406, as shown in FIG. 4. Such snapping places the interior of the inner tube 406 in fluid communication with the applicator 402, so that the oral care composition 408 is able to flow from the interior of the inner tube 406 and along an inner side of the outer tube 405 to a surface 403 of the applicator 402, without reaching an outer surface of the outer tube 405, i.e. an outer surface of the storage portion 404. The user then holds the outer tube 405 of the storage portion 404 between their fingers, without their fingers coming into contact with the oral care composition 408, and rubs the surface 403 of the applicator 402 on their teeth in order to apply the oral care composition 408 to their teeth. After a single use of the oral care device 400, the user can dispose of the remains of the oral care device 400.

In the embodiment of FIG. 4, the applicator 402 is made from a porous material. In a variation to the embodiment of FIG. 4, the applicator 402 is not made from a porous material, but instead comprises a member with one or more channels defined therein for carrying the oral care composition 408 from the interior of the inner tube 406 and through the outer tube 405 to the surface 403 of the applicator 402.

In a variation to the embodiment of FIG. 4, as shown in FIG. 5 there is provided a breakable seal 401 between the interior of the sealed inner tube 406 and the applicator 402. A user is able to apply a force to the sealed inner tube 406 of the oral care device 400 in order to compress the inner tube 406, thereby to increase the pressure of the oral care composition 408 in the interior of the inner tube 406. This increase in pressure causes the seal 401 to break, which places the interior of the inner tube 406 in fluid communication with the applicator 402, so that the oral care composition 408 is able to flow from the interior of the inner tube 406 and through the outer tube 405 to the surface 403 of the applicator 402.

In a variation to the embodiment of FIG. 5, as shown in FIG. 6 material of the oral care device 400 is twistably deformable at a position between the interior of the sealed inner tube 406 and the applicator 402 in order to break the seal 401. This again places the interior of the inner tube 406 in fluid communication with the applicator 402, so that the oral care composition 408 is able to flow from the interior of the inner tube 406 and through the outer tube 405 to the surface 403 of the applicator 402.

In another embodiment of the present invention, as shown in FIG. 7, each of the plurality of oral care devices 400 comprises a front sheet or film 510, a backing sheet 520, and a strip 530 holding the oral care composition 538. The front sheet 510 and the backing sheet 520 are sealed together with the strip 530 therebetween, so that the front sheet 510 and backing sheet 520 together isolate the strip 530 and the oral care composition 538 held by the strip 530 from an exterior of the oral care device 400. In this way, each of the strips 530 is individually wrapped by the front sheet 510 and the backing sheet 520. The oral care composition 538 may be held within pores of the strip 530, or the oral care composition 538 may be held on a surface of the strip 530. To use one of the strips 530, a user peels the front sheet 510 from the backing sheet 520 to expose the strip 530, and then the user applies the strip 530 onto their teeth for a predetermined period of time, as is known in the art, to apply the oral care composition 538 to their teeth. After a single use of the strip 530, the user can dispose of the remains of the oral care device 400.

Figure 8:
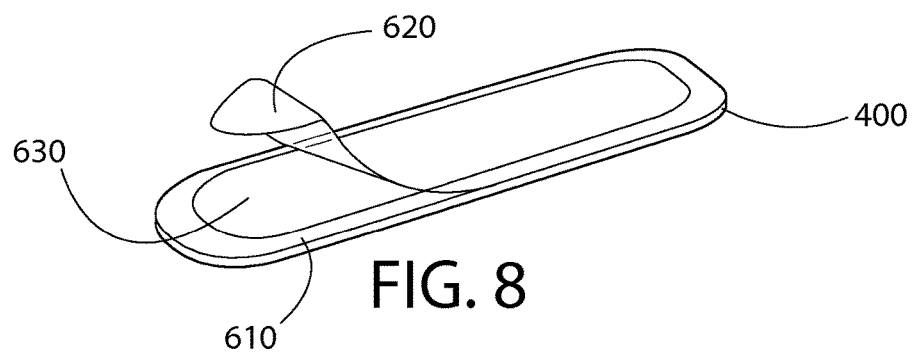
FIG. 8 shows a perspective view of a further alternative oral care device for use in the system of FIG. 1.
Figure 9:
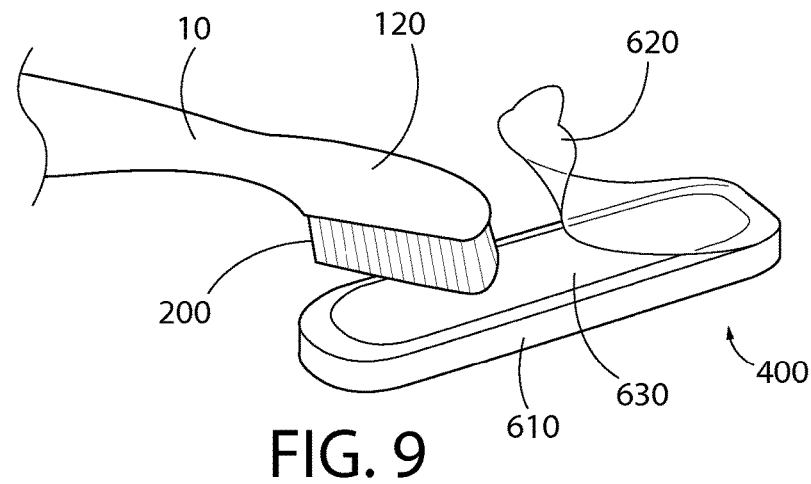
FIG. 9 shows a perspective view of oral care elements of the oral care implement of the system of claim 1 inserted into an oral care composition held be the oral care device of FIG. 8.

In another embodiment of the present invention, as shown in FIG. 8, each of the plurality of oral care devices 400 comprises a vessel in the form of a tray 610 having an interior within which the oral care composition 630 is held. The tray 610 is sealed by a removable lid, film or sheet 620, to isolate the oral care composition 630 held by the tray 610 from an exterior of the oral care device 400. To use one of the devices 400, a user peels the lid, film or sheet 620 from the tray 610 to expose the oral care composition 630, and then the user inserts the oral care elements 200 of the toothbrush 10 into the oral care composition 630 to apply the oral care composition 630 to the oral care elements 200, as shown in FIG. 9. The user then rubs the oral care elements 200 onto their teeth to apply the oral care composition 630 to their teeth. After a single use of the tray 610 and its contents, the user can dispose of the remains of the oral care device 400.

In variations to the illustrated embodiments, the cavity 114 may be provided elsewhere in the body 100 than at the position shown in the Figures. For example, the cavity 114 may be provided in the handle 110 away from the proximal end 111 of the handle 110, such as in or adjacent to the neck portion 118 of the handle 110. In some variations to the illustrated embodiment, the handle 110 may define an opening 113 of the cavity 114 away from the proximal end 111 of the handle 110, such as in or adjacent to the neck portion 118 of the handle 110 or at the distal end 112 of the handle 110. In some variations to the illustrated embodiment, the cavity may be in the head 120 of the body 100 and the head 120 may define an opening of the cavity. In some variations to the illustrated embodiment, the cavity may be in both the handle 110 and the head 120 of the body 100. An opening into such a cavity in both the handle 110 and the head 120 may be defined by the handle 110 or by the head 120. In some embodiments, a plurality of cavities may be provided in the body 100, and respective openings of the cavities may be defined by the handle 110 and/or by the head 120.

In some variations to the illustrated embodiment, the cap 300 is connected to the body 100 via a hinge, and the cap 300 is movable relative to the body 100 between a first position, at which the cap 300 blocks the opening 113, and a second position, at which the opening 113 is not blocked by the cap 300. In some such variations to the illustrated embodiment, the cap 300 may be unitary with the body 100, with the cap 300 connected to the body 100 via a living hinge.

Each of the oral care devices 400 discussed above is dentifrice-free. In respective variations to the oral care devices 400 shown in FIGS. 3 to 6, each of the respective oral care compositions held in the interior of the sealed vessel of the respective oral care device 400 shown in FIGS. 3 to 6 comprises a dentifrice, such as a toothpaste.

What is claimed:
1. An oral care system, comprising:
   an oral care implement, comprising:
      a body comprising a handle and a head at an end of the handle, the head having at least one oral care element extending therefrom, and
      a cavity in the body, the body defining a proximally facing opening of the cavity at a proximal end of the handle opposite the head; and
   a plurality of dentifrice-free oral care devices in the cavity, each of the oral care devices comprising:

an oral care composition comprising an oral care agent;
a storage portion comprising a sealed vessel having an interior holding the oral care composition comprising the oral care agent; and
an applicator;
wherein the sealed vessel or a seal thereof is breakable to place the interior of the vessel in fluid communication with the applicator.

2. The oral care system of claim 1, wherein each of the oral care devices comprises a predetermined dose or volume of the oral care agent comprised in the oral care device.

3. The oral care system of claim 1, wherein each of the oral care devices comprises the same oral care composition.

4. The oral care system of claim 1, wherein each of the oral care devices is a single-use device.

5. The oral care system of claim 1, wherein each of the oral care devices is sealed to isolate the oral care composition from an exterior of the oral care device.

6. The oral care system of claim 5, wherein each of the oral care devices is sealed by a removable lid, film or sheet, to isolate the oral care composition from an exterior of the oral care device.

7. The oral care system of claim 1, wherein the sealed vessel comprises an inner tube, and wherein the storage portion comprises an impermeable outer tube disposed around the inner tube, and wherein the interior is an interior of the inner tube.

8. The oral care system of claim 1, wherein the applicator is made from a porous material, or wherein the applicator comprises a member with one or more channels defined therein for carrying the oral care composition.

9. The oral care system of claim 1, wherein the oral care device is twistably deformable or the vessel is snappable, in order to place the interior of the vessel in fluid communication with the applicator.

10. The oral care system of claim 1, wherein the oral care implement comprises a cap movable relative to the body between a first position, at which the cap blocks the opening, and a second position, at which the opening is not blocked by the cap.

11. The oral care system of claim 10, wherein the cap is detached from the body when the cap is at the second position.

12. The oral care system of claim 10, wherein the cap is attached to the body when the cap is at the first position.

13. The oral care system of claim 1, wherein the oral care implement is a toothbrush.

* * * * *